(12) United States Patent
Kobayashi et al.

(10) Patent No.: US 10,463,319 B2
(45) Date of Patent: Nov. 5, 2019

(54) COMPRESSION PLATE, X-RAY DIAGNOSTIC APPARATUS AND METHOD OF MANUFACTURING THE COMPRESSION PLATE

(71) Applicant: Toshiba Medical Systems Corporation, Otawara-shi (JP)

(72) Inventors: Yoshimasa Kobayashi, Nasushiobara (JP); Takehito Tomaru, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 195 days.

(21) Appl. No.: 15/787,770

(22) Filed: Oct. 19, 2017

(65) Prior Publication Data

US 2018/0110484 A1   Apr. 26, 2018

(30) Foreign Application Priority Data

Oct. 20, 2016  (JP) .................................. 2016-206219

(51) Int. Cl.
*A61B 6/04* (2006.01)
*A61B 6/00* (2006.01)

(52) U.S. Cl.
CPC .......... *A61B 6/0414* (2013.01); *A61B 6/4488* (2013.01); *A61B 6/502* (2013.01)

(58) Field of Classification Search
CPC ................................... A61B 6/04; A61B 6/00
See application file for complete search history.

(56) References Cited

U.S. PATENT DOCUMENTS 5,161,273 A * 11/1992 Deck ........................ A47D 9/00
                                                        5/601
5,553,111 A *  9/1996 Moore .................. A61B 6/0414
                                                      378/208
5,657,367 A *  8/1997 Couch .................. A61B 6/0421
                                                      378/167
5,664,573 A *  9/1997 Shmulewitz ........... A61B 6/502
                                                      128/915
5,754,997 A *  5/1998 Lussi ....................... A61B 6/04
                                                        5/601

(Continued)

FOREIGN PATENT DOCUMENTS

JP       2003-525681       9/2003
JP       2009-207534       9/2009

(Continued)

*Primary Examiner* — Marcus H Taningco
*Assistant Examiner* — Djura Malevic
(74) *Attorney, Agent, or Firm* — Oblon, McClelland, Maier & Neustadt, L.L.P.

(57) ABSTRACT

According to one embodiment, a compression plate compresses a breast of a subject with the breast between the compression plate and an imaging plane of an imaging table. The compression plate including a compression face and a chest wall face. The compression face is configured to compress the breast to the imaging table. The chest wall face is configured continuously from the compression face to be in contact with a chest wall of the subject during X-ray imaging. The chest wall face includes a second region which is in contact with the chest wall of the subject, and the second region has surface roughness which is greater than that of a first region of the compression face, which is opposed to the imaging table.

10 Claims, 10 Drawing Sheets

(56) References Cited

U.S. PATENT DOCUMENTS

| | | | | |
|---|---|---|---|---|
| 5,833,627 | A * | 11/1998 | Shmulewitz | A61B 8/0833 600/562 |
| 5,851,180 | A * | 12/1998 | Crosby | A61B 6/0414 600/407 |
| 5,891,074 | A * | 4/1999 | Cesarczyk | A61F 13/0203 128/109.1 |
| 6,049,583 | A * | 4/2000 | Galkin | A61B 6/0414 378/207 |
| 6,968,033 | B2 * | 11/2005 | Lebovic | A61B 6/0414 378/37 |
| 7,502,441 | B2 * | 3/2009 | Lebovic | A61B 6/0414 378/37 |
| 7,616,732 | B2 * | 11/2009 | Lebovic | A61B 6/0414 378/37 |
| 8,098,793 | B2 * | 1/2012 | Lebovic | A61B 6/0414 378/37 |
| 8,705,689 | B2 * | 4/2014 | Lebovic | A61B 6/0414 378/37 |
| 9,504,433 | B2 * | 11/2016 | Lebovic | A61B 6/0414 |
| 9,936,925 | B2 * | 4/2018 | Lebovic | A61B 6/0414 |
| 2003/0174807 | A1 * | 9/2003 | Lebovic | A61B 6/0414 378/37 |
| 2006/0126794 | A1 | 6/2006 | Hermann et al. | |
| 2006/0239399 | A1 * | 10/2006 | Lebovic | A61B 6/0414 378/37 |
| 2009/0220055 | A1 * | 9/2009 | Nakata | A61B 6/0414 378/208 |
| 2010/0046698 | A1 * | 2/2010 | Lebovic | A61B 6/0414 378/37 |
| 2012/0114096 | A1 * | 5/2012 | Lebovic | A61B 6/0414 378/37 |
| 2012/0136235 | A1 * | 5/2012 | Taku | A61B 5/0095 600/407 |
| 2014/0307848 | A1 * | 10/2014 | Lebovic | A61B 6/0414 378/37 |
| 2015/0157282 | A1 * | 6/2015 | Kobayashi | A61B 6/502 378/37 |
| 2016/0051207 | A1 * | 2/2016 | Timberg | A61B 6/0414 378/62 |
| 2016/0296186 | A1 * | 10/2016 | Hugg | A61B 6/0414 |
| 2017/0071555 | A1 * | 3/2017 | Lebovic | A61B 6/0414 |
| 2017/0172531 | A1 * | 6/2017 | Sugiyama | A61B 6/502 |
| 2017/0338108 | A1 * | 11/2017 | Yamazaki | H01L 21/28211 |
| 2017/0360389 | A1 * | 12/2017 | Ochiai | A61B 6/54 |
| 2018/0040722 | A1 * | 2/2018 | Obonai | H01L 21/02359 |
| 2018/0273597 | A1 * | 9/2018 | Stimson | A61K 38/212 |
| 2018/0289341 | A1 * | 10/2018 | Lebovic | A61B 6/0414 |
| 2018/0337039 | A1 * | 11/2018 | Yamazaki | H01L 21/28211 |
| 2018/0338795 | A1 * | 11/2018 | Sugiyama | A61B 34/10 |

FOREIGN PATENT DOCUMENTS

| | | |
|---|---|---|
| JP | 2009-207561 | 9/2009 |
| JP | 2012-115334 | 6/2012 |
| JP | 2013-013775 | 1/2013 |

* cited by examiner

COMPRESSION PLATE, X-RAY DIAGNOSTIC APPARATUS AND METHOD OF MANUFACTURING THE COMPRESSION PLATE

CROSS-REFERENCE TO RELATED APPLICATION

This application is based upon and claims the benefit of priority from prior Japanese Patent Application No. 2016-206219, filed Oct. 20, 2016, the entire contents of which are incorporated herein by reference.

FIELD

Embodiments described herein relate generally to a compression plate, an X-ray diagnostic apparatus and a method of manufacturing the compression plate.

BACKGROUND

A transparent resin compression plate is used for positioning in mammography. For the positioning, a radiology technician thins and evens out a breast of a subject with his or her hands and broadens the mammary glands. To keep this condition, the radiology technician fixes the breast using the compression plate.

The present inventor studied the conventional compression plate and found that there was room for improvement in the compression plate in the following respect, though no particular problem occurs when it is normally used.

The transparent resin compression plate may stick to the skin of the chest wall of a subject because its surface is slick. When the compression plate moves down, it is likely that the skin of the chest wall will be pulled downward, which can inflict pain on the subject and cause the skin to peel. Since the conventional compression plate may stick to the skin of the chest wall, it can be improved.

The object is to provide a compression plate which does not stick to the skin of the chest wall of a subject to relieve the subject of pain when the compression plate moves down, an X-ray diagnostic apparatus including the compression plate, and a method of manufacturing the compression plate.

DETAILED DESCRIPTION

In general, according to one embodiment, a compression plate compresses a breast of a subject with the breast between the compression plate and an imaging plane of an imaging table. The compression plate including a compression face and a chest wall face.

The compression face is configured to compress the breast to the imaging table.

The chest wall face is configured continuously from the compression face to be in contact with a chest wall of the subject during X-ray imaging. The chest wall face includes a second region which is in contact with the chest wall of the subject, and the second region has surface roughness which is greater than that of a first region of the compression face, which is opposed to the imaging table.

The embodiments will be described below with reference to the accompanying drawings. In the following description, the "X-ray diagnostic apparatus" can be called "a mammography apparatus" or "a breast X-ray diagnostic apparatus." The "region whose surface roughness is greater than that of the first region" can be called "a minute uneven region," "an uneven region," "a translucent region," "a milk-white region," "a low-friction region," "a dry region" or "a smooth region."

First Embodiment

Figure 1:
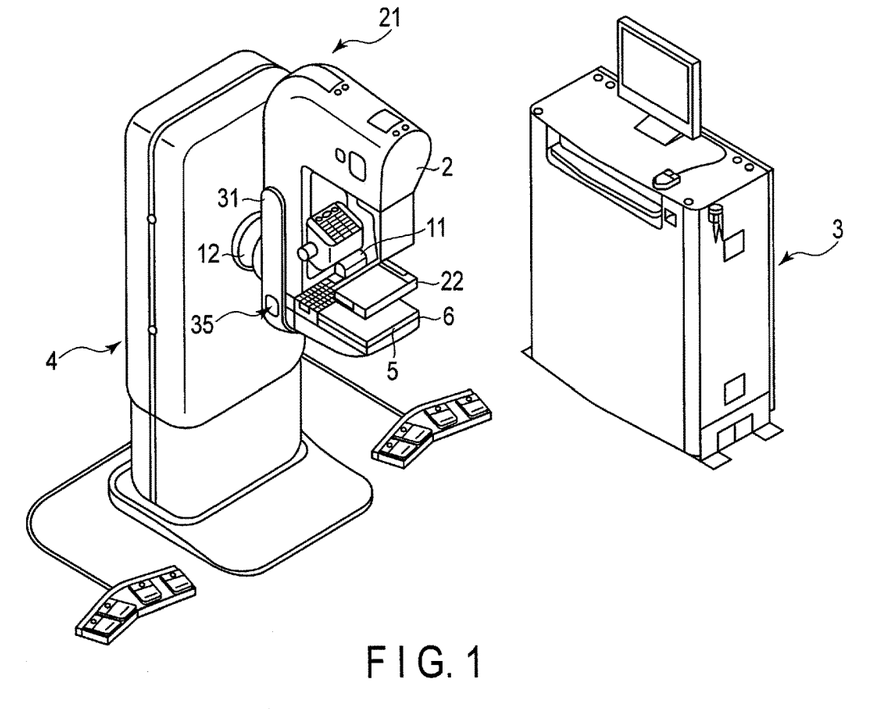
FIG. 1 is a schematic external view of an X-ray diagnostic apparatus according to a first embodiment.

FIG. 1 shows the outward appearance of an X-ray diagnostic apparatus according to a first embodiment. The X-ray diagnostic apparatus includes an imaging table 6 having an imaging plane to which a subject's breast is compressed and a compression plate 22 to compress the subject's breast with the breast between the imaging plane of the imaging table 6 and the compression plate 22, as elements for mammography positioning. The X-ray diagnostic apparatus also includes a stand 4. The stand 4 is supported by a horizontal column 12 such that a substantially L-shaped or I-shaped arm 21 can be rotated on the central axis of the horizontal column 12. The rotation of the arm 21 allows imaging such as CranioCaudal projection (CC) and MedioLateral Oblique projection (MLO). An X-ray tube 2 is attached to one end of the arm 21. The X-ray tube 2 is covered with a housing. A high-voltage generator 3 is electrically connected to the stand 4. The high-voltage generator 3 applies a high voltage (tube voltage) between electrodes of the X-ray tube 2 and supplies a filament current to a filament. Accordingly, the X-ray tube 2 generates an X ray. Note that an operating console can be provided on the high-voltage generator 3.

The imaging table 6 is attached to the other end of the arm 21. An X-ray detector 5 is contained in the imaging table 6 opposite to the imaging plane of the imaging table 6. As the X-ray detector 5, a film cassette, a CR cassette or a flat panel detector (FPD) is employed. The X-ray detector 5 is disposed opposite to the X-ray tube 2 to detect an X ray that has transmitted the subject's compressed breast.

The arm 21 is equipped with a compression mechanism 11. The compression mechanism 11 is a movement mechanism including a motor to move the compression plate 22 in the vertical direction. The compression plate 22 is formed of thermoplastic resin and moves in the vertical direction away from and close to the imaging table 6 in parallel with the imaging table 6. When the compression plate 22 moves downward, the subject's breast is compressed between the compression plate 22 and the imaging plane of the imaging table 6. As the thermoplastic resin of the compression plate 22, for example, polycarbonate having a high mechanical strength and transmitting X rays can be used. The compression plate 22 compresses the breast, which has been thinned and evened out by the hand of a radiology technician, to the imaging table 6, with the result that the breast is fixed in a thin and even state. The movement of the compression plate 22 and the rotation of the arm 21 can be performed if the radiology technician operates the operation button of an operation panel 35 provided on an arm rest 31. The arm rest 31 is shaped like a "U" to surround the arm 21 between the imaging table 6 and the horizontal column 12.

The foregoing compression plate 22 used in the X-ray diagnostic apparatus will be described in detail below.

Figure 2:
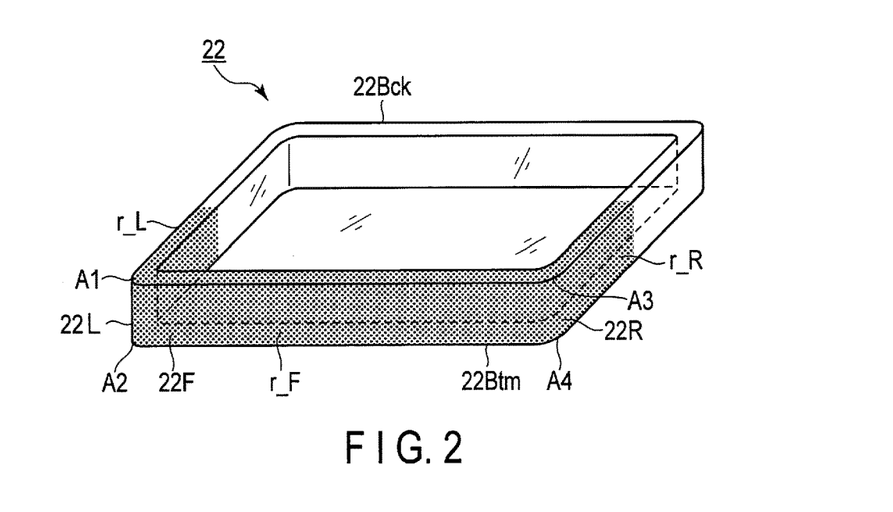
FIG. 2 is a schematic external view of a compression plate according to the first embodiment.
Figure 3A:
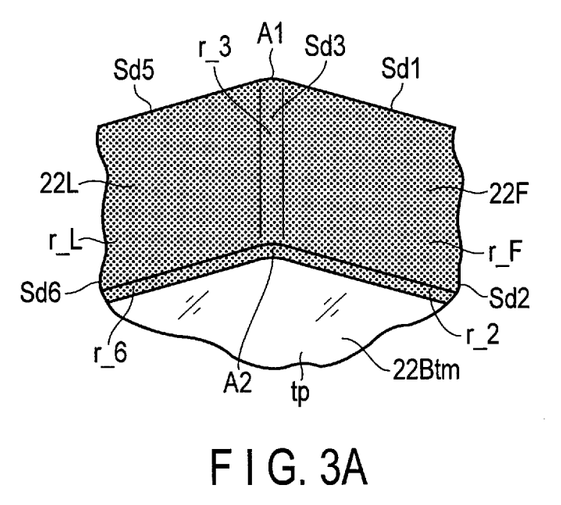
FIG. 3A is a schematic external view of a first top and its periphery of the compression plate according to the first embodiment.
Figure 3B:
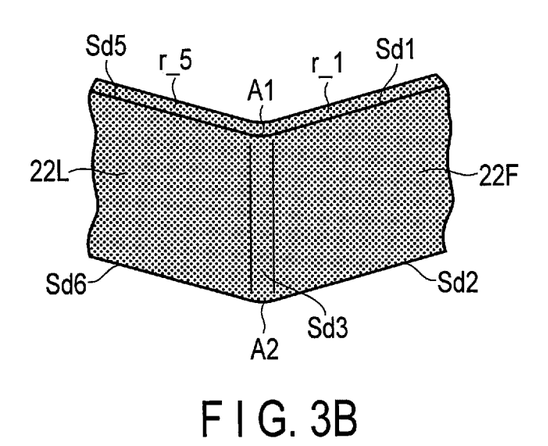
FIG. 3B is a schematic external view of a second top and its periphery of the compression plate according to the first embodiment.
Figure 3C:
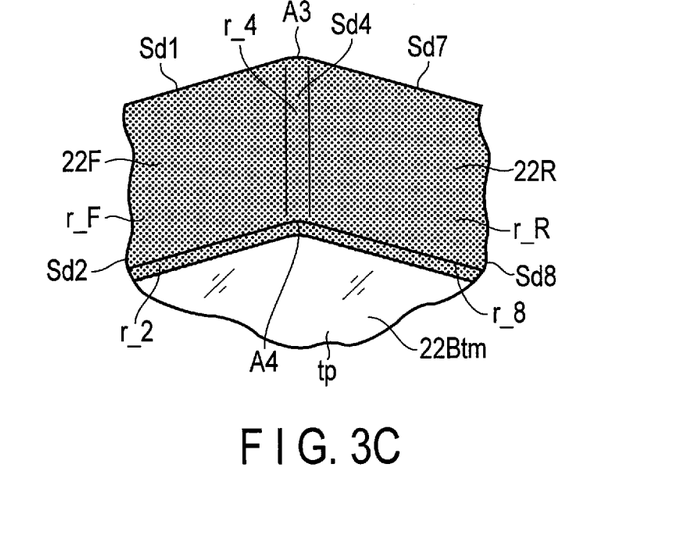
FIG. 3C is a schematic external view of a third top and its periphery of the compression plate according to the first embodiment.
Figure 3D:
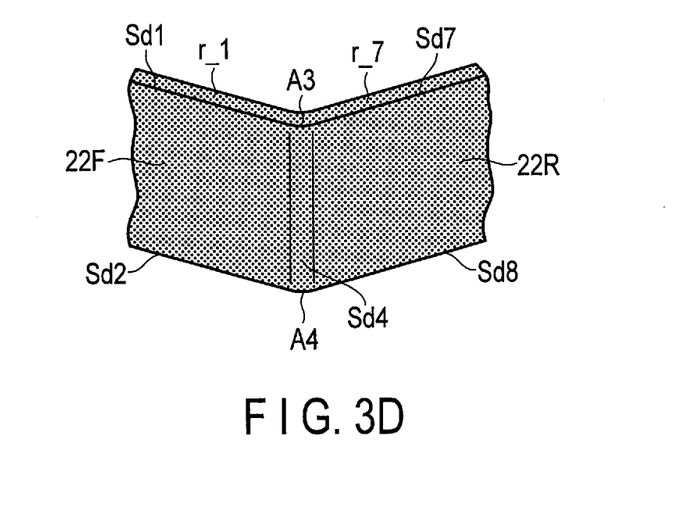
FIG. 3D is a schematic external view of a fourth top and its periphery of the compression plate according to the first embodiment.

FIG. 2 is a schematic external view of the foregoing compression plate 22, and FIGS. 3A to 3D are schematic external views showing the respective tops and their peripheries of the compression plate 22. The compression plate 22 is generally shaped like a box with no lid, i.e., five faces. More specifically, the compression plate 22 has a compression face 22Btm opposed to the imaging plane of the imaging table 6, a chest wall face 22F opposed to the subject's chest wall, a back face 22Bck opposed to the chest wall face 22F, and a plurality of side faces 22L and 22R located between the chest wall face 22F and the back face 22Bck. The chest wall face 22F is shaped substantially like a rectangle with long sides that are substantially parallel to the imaging plane of the imaging table 6 and includes a region (second region) r_F whose surface roughness is greater than that of a transparent region (first region) tp of the compression face 22Btm, the region r_F being in contact with the chest wall. As the first region, a translucent region can be used in place of the transparent region tp. The side face 22L is located on the left side when viewed from the subject during CranioCaudal (CC) projection. The side face 22R is located on the right side when viewed from the subject during CC projection. The side faces 22L and 22R may respectively include regions (third and fourth regions) r_L and r_R whose surface roughness is greater than that of the transparent region tp. The chest wall face 22F has tops A1 to A4 at four corners thereof and sides Sd to Sd4 between the corresponding tops. The top A1 is located on the upper left side when viewed from the subject during CC projection, and the top A2 is located on the lower left side when viewed from the subject during CC projection. The top A3 is located on the upper right side when viewed from the subject during CC projection, and the top A4 is located on the lower right side when viewed from the subject during CC projection. The side Sd1 is located between the tops A1 and A3, and the side Sd2 is located between the tops A2 and A4. The side Sd3 is located between the tops A1 and A2, and the side Sd4 is located between the tops A3 and A4. The tops A1 to A4 and the sides Sd1 to Sd4 are each rounded. The tops A1 to A4 and the sides Sd1 to Sd4 may include regions r_1 to r_4 whose surface roughness is greater than that of the transparent region tp of the compression face 22Btm.

The compression face 22Btm compresses the breast to the imaging table 6. The compression face 22Btm includes a transparent region tp opposed to the imaging table 6. The transparent region tp may include a path (referred to as an X-ray path hereinafter) which transmits X rays. The compression face 22Btm may also include a region (fourth region) whose surface roughness is greater than that of the transparent region tp in a region other than the X-ray path.

The chest wall face 22F is formed continuously from the compression face 22Btm and brought into contact with the chest wall of the subject during X-ray imaging. The chest wall face 22F that is brought into contact with the chest wall includes a region r_F whose surface roughness is greater than that of the transparent region tp opposed to the imaging table 6 of the compression face 22Btm. For example, as regards the arithmetic average roughness, the surface roughness of the region r_F has only to fall within a range of 0.1 μm to 2 μm and favorably a range of 0.4 μm to 1 μm, considering that no skin is pulled when the compression plate 22 moves down. As the arithmetic average roughness, for example, a contact needle scanning type surface roughness measurement device (e.g., SURFCOM™ 1500DX3-12 of Tokyo Seimitsu Co., Ltd.) is used to measure the surface roughness on the basis of JIS (Japanese Industrial Standards)-B0601:2001. For example, five to ten measurement points can be chosen for the average. If the surface roughness falls within the above range, the area of contact with the subject's skin decreases moderately. Thus, the surface is dried and the subject's skin is smoothed when the compression plate 22 is moved down, with the result that the skin is not pulled. If the surface roughness does not reach the lower limit, the surface will be smoothed and the compression plate 22 will stick to the subject's skin when it is moved down, with the result that the skin is likely to be pulled. If the surface roughness exceeds the upper limit, the surface becomes rough and the subject's skin is rubbed or scraped when the compression plate 22 moves down, with the result that the subject is likely to feel uncomfortable and pain.

It is favorable that the chest wall face 22F be thin in order to pick up an image of the root of a breast Pb while decreasing the degree of pulling out the breast Pb. For example, it is favorable that the chest wall face 22F be thinner than each of the side faces 22R and 22L. Similarly, it is favorable that the chest wall face 22F be thinner than the back face 22Bck.

The side faces 22L and 22R are formed continuously from the compression face 22Btm and the chest wall face 22F along a direction orthogonal to the compression face 22Btm and the chest wall face 22F. The side faces 22L and 22R may respectively include regions r_L and r_R whose surface roughness is greater than that of the transparent region tp. The region r_L need not be formed on the entire surface of the side face 22L or the region r_R need not be formed on the entire surface of the side face 22R. The regions r_L and r_R have only to be formed in a region that could be in contact with the upper arms of the subject P. For example, the regions r_L and r_R have only to be formed in a region close to the chest wall face 22F rather than a central region between the chest wall face 22F and the back face 22Bck. The regions r_L and r_R whose surface roughness is greater are translucent regions or milk-white regions and their outward appearances look like ground glass. Thus, when the regions and r_R are formed on the side faces 22L and 22R, respectively, the subject feels her upper arms are dry and the subject's breast is hard to see, thus making it possible to lessen a sense of shame of the subject.

The region r_F in the chest wall face 22F and each of the regions r_L and r_R in the side faces 22L and 22R can be formed continuously to each other. In other words, the sides Sd3 and Sd4 on the border of the side faces 22L and 22R and the chest wall face 22F may include regions r_3 and r_4 whose surface roughness is greater than that of the transparent region tp at the roundish corners. Each of the side faces 22L and 22R is shaped substantially like a rectangle with long sides that are substantially parallel to the imaging plane of the imaging table 6. Each of the side faces 22L and 22R has tops at four corners of the rectangle and sides between the corresponding tops. Of the sides of the side face 22L, sides Sd5 and Sd6 that are substantially parallel to the imaging plane of the imaging table 6 may include regions r_5 and r_6 whose surface roughness is greater than the transparent region tp at the roundish corners. Note that the side Sd5 is located on the upper left side when viewed from the subject during CC projection and the side Sd6 is located on the lower left side when viewed from the subject during CC projection. Similarly, of the sides of the side face 22R, sides Sd7 and Sd8 that are substantially parallel to the imaging plane of the imaging table 6 may include regions r_7 and r_8 whose surface roughness is greater than the transparent region tp at the roundish corners. Note that the side Sd7 is located on the upper right side when viewed from the subject during CC projection and the side Sd8 is located on the lower right side when viewed from the subject during CC projection.

Figure 4:
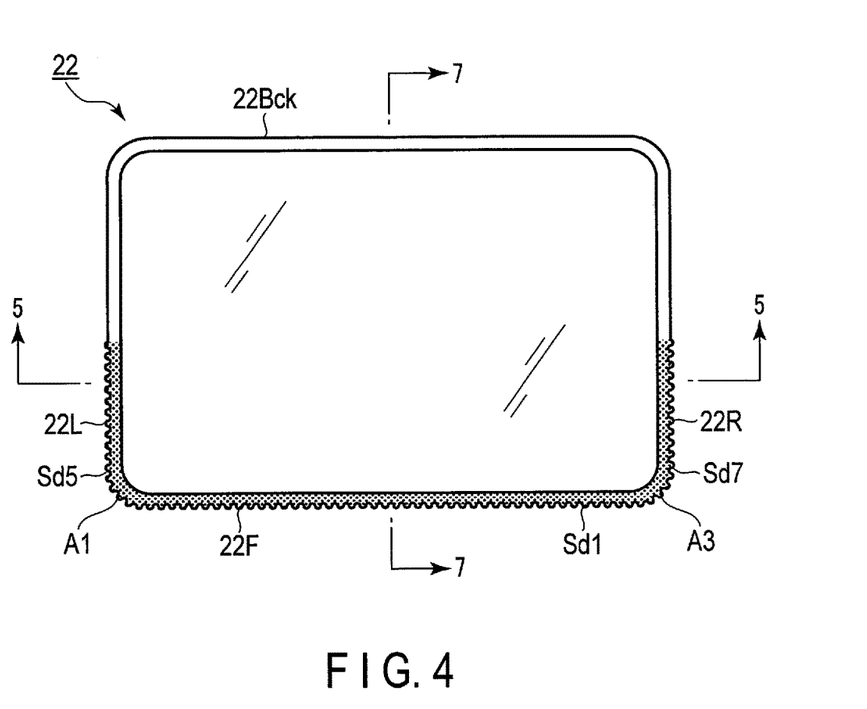
FIG. 4 is a schematic top view showing a configuration of the compression plate according to the first embodiment.
Figure 5:
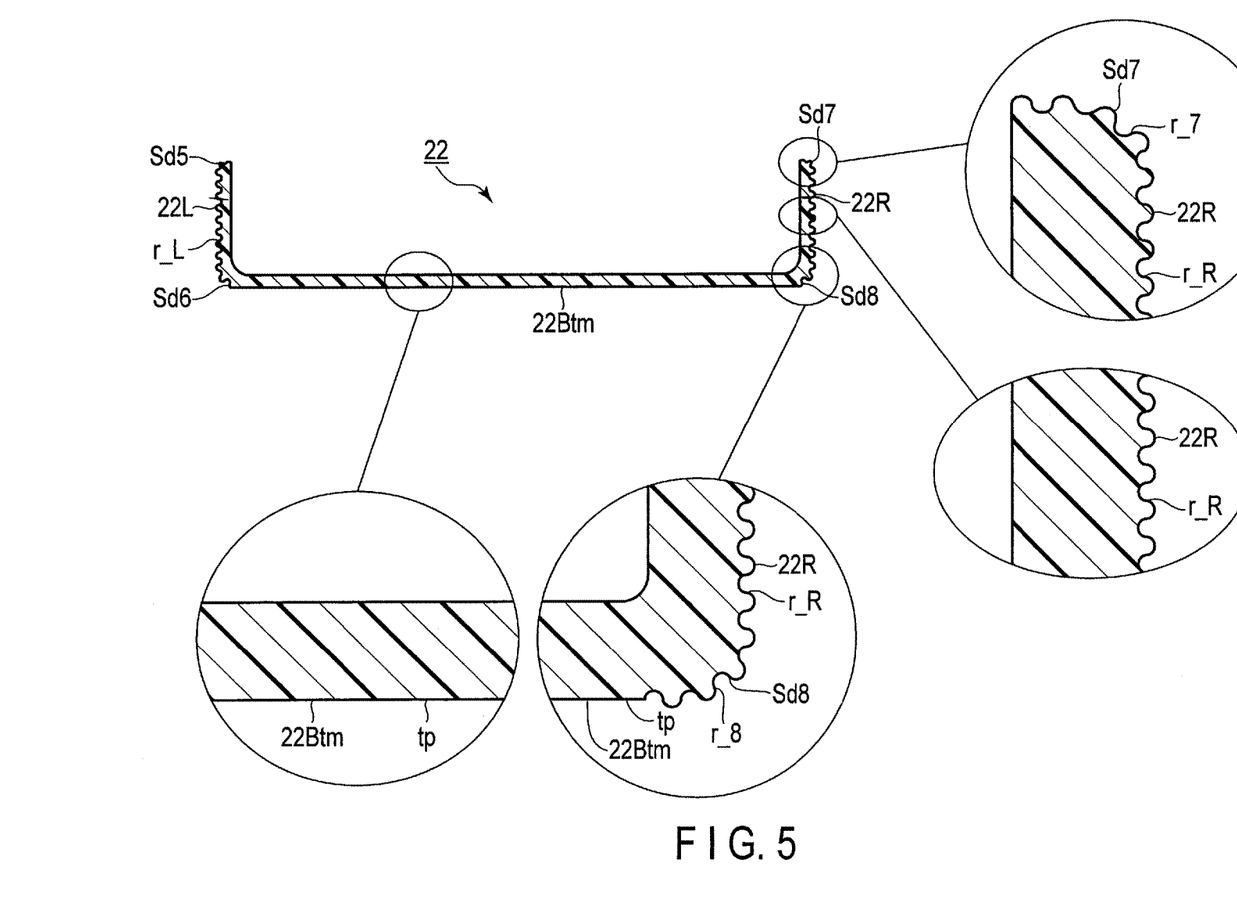
FIG. 5 is a cross-sectional view taken along line 5-5 in FIG. 4, including an enlarged view of each section of the compression plate according to the first embodiment.
Figure 6:
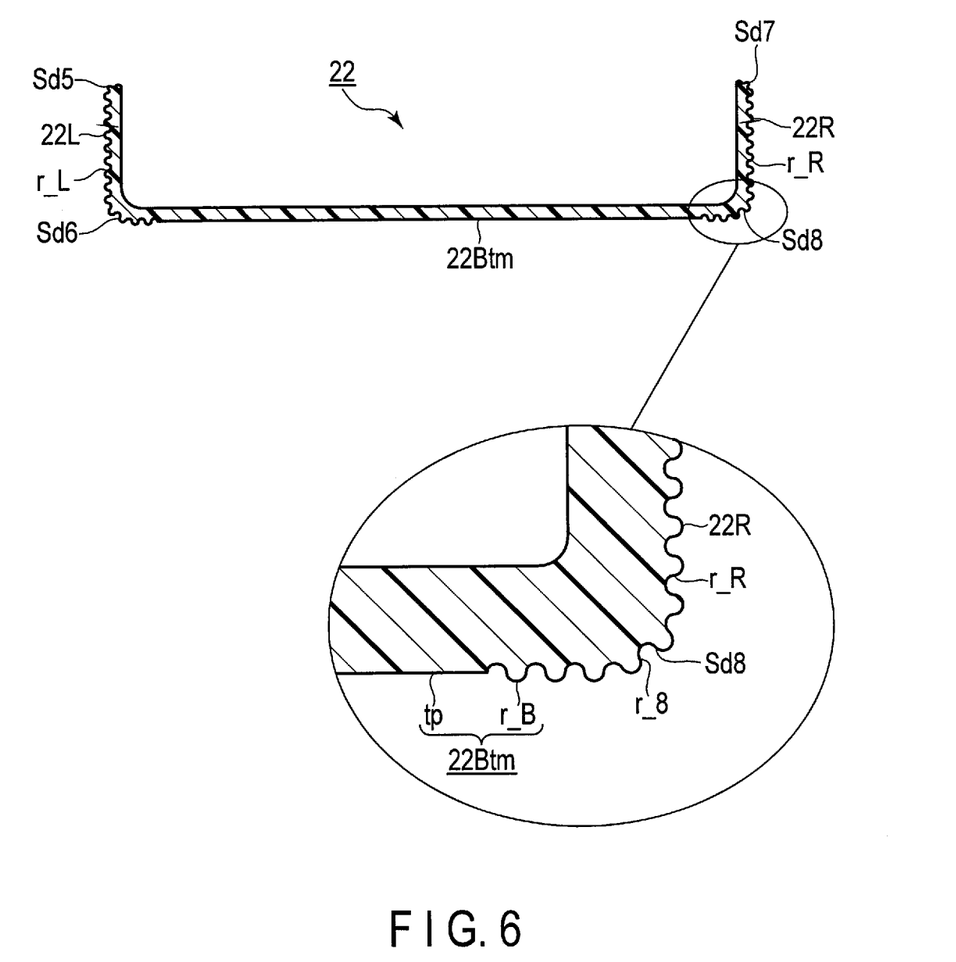
FIG. 6 is a schematic view showing a modification to the compression plate shown in FIG. 5.
Figure 7:
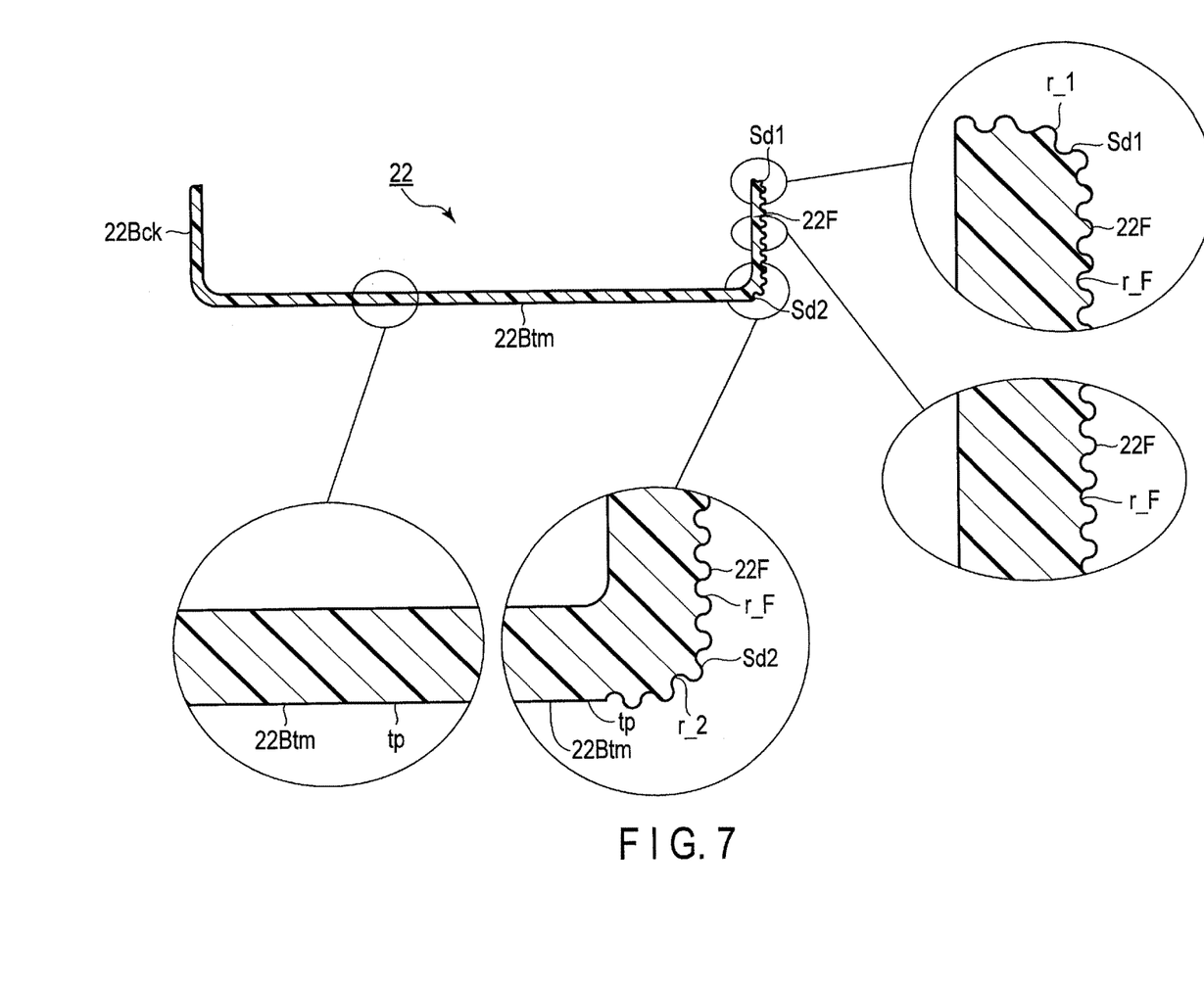
FIG. 7 is a cross-sectional view taken along line 7-7 in FIG. 4, including an enlarged view of each section of the compression plate according to the first embodiment.

FIG. 4 is a schematic top view showing a configuration of the compression plate 22. FIG. 5 is a cross-sectional view taken along line 5-5 in FIG. 4, including an enlarged view of each section of the compression plate 22. FIG. 6 is a schematic view showing a modification to the compression plate shown in FIG. 5. FIG. 7 is a cross-sectional view taken along line 7-7 in FIG. 4, including an enlarged view of each section of the compression plate 22.

As shown in FIG. 5, the side face 22R and the sides Sd7 and Sd8 can be formed by continuing the regions r_R, r_7 and r_8 whose surface roughness is greater than that of the transparent region tp. Similarly, the side face 22L and the sides Sd5 and Sd6 can be formed by continuing the regions r_L, r_5 and r_6 whose surface roughness is greater than that of the transparent region tp.

As shown in FIG. 6, the compression face 22Btm may include not only the transparent region tp but also a region r_B whose surface roughness is greater than that of the transparent region tp. The region r_B can be formed continuously from the regions r_R and r_8 whose surface roughness is greater than that of, e.g. the side face 22R and the side Sd8. Similarly, though not shown, the region r_B whose surface roughness is greater than that of the compression surface 22Btm can be formed continuously from the regions r_L and r_6 whose surface roughness is greater than that of the side face 22L and the sides Sd6. It is favorable that the region r_B with great surface roughness be formed in a region other than the X-ray path because it appears as an X-ray image. Even though the region r_B with great surface roughness is formed in an X-ray path within the compression face 22Btm, it is favorable that it be formed in a region that is not in contact with the subject's breast.

As shown in FIG. 7, the chest wall face 22F and the sides Sd1 and Sd2 can be formed by continuing the regions r_F, r_1 and r_2 whose surface roughness is greater than that of the transparent region tp. The side Sd2, which is located on the border between the compression face 22Btm and the chest wall face 22F and which is in contact with the root of the breast, may include a region (fifth region) r_2 whose surface roughness is greater than that of the transparent region tp at the roundish corner. In contrast, the transparent region tp is formed all over the back face 22Bck. The back face 22Bck may include a region whose surface roughness is greater than that of the transparent region tp. Since, however, the back face 22Bck is not brought into contact with the subject while the compression plate 22 is moving down, it need not include a region with great surface roughness. Furthermore, the back face 22Bck and the side faces 22L and 22R may include, e.g., a hole portion, a groove portion and a claw portion (neither of which is shown) by which the compression mechanism 11 holds the compression plate 22.

An operation of the X-ray diagnostic apparatus having a compression plate configured as described above will be described with reference to FIGS. 8 and 9. In the following description, a positioning operation of the compression plate 22 that is moving down and moving close to the imaging table, will be chiefly described.

Figure 8:
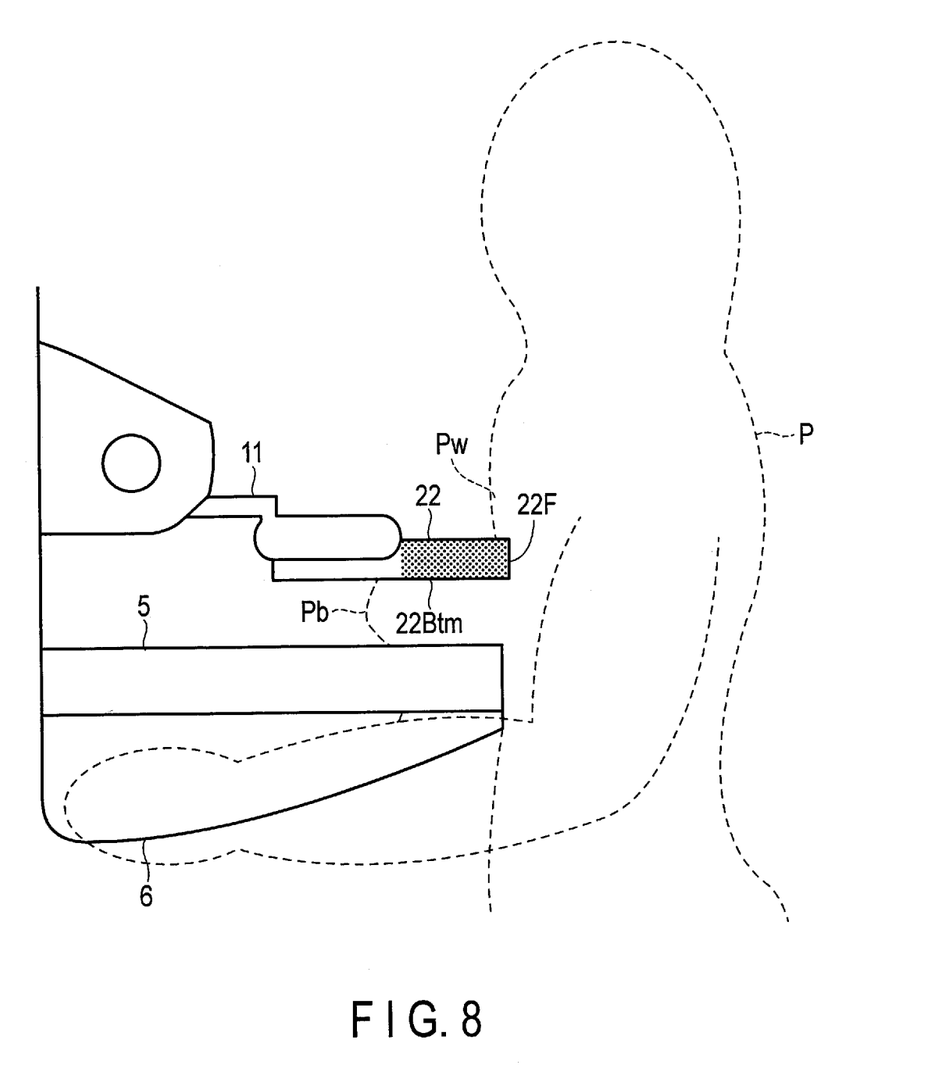
FIG. 8 is a schematic view illustrating an operation of the X-ray diagnostic apparatus according to the first embodiment.

First, the X-ray diagnostic apparatus receives an instruction about the imaging direction (MLO or CC direction) of the breast Pb of the subject P from the radiology technician. Assume here that the CC direction is designated as the imaging direction.

Then, the X-ray diagnostic apparatus reads information input by a radiology technician's operation of the operation panel 35 and adjusts the angle and height of the arm 21 in accordance with the imaging direction and the height of the breast Pb.

Then, as shown in FIG. 8, the radiology technician positions the breast Pb of the subject P on the imaging table 6. During the positioning for CC projection, the compression plate 22 is moved down with the breast Pb between the compression plate 22 and the imaging plane (X-ray detector 5).

The compression plate 22 moves down while its chest wall face 22F slides on the chest wall Pw through the region r_F whose surface roughness is greater than that of the transparent region tp. In other words, while the compression plate 22 is moving down, the chest wall face 22F does not pull the skin of the chest wall Pw downward, with the result that the subject P can be relieved of pain.

Furthermore, the side faces 22L and 22R of the compression plate 22 makes it difficult to see the breast Pb from its obliquely upper right side or obliquely upper left side; consequently, a sense of shame of the subject P can be lessened.

After the compression plate 22 moves down, the radiology technician puts his or her hand between the compression plate 22 and the breast Pb to flatten the breast Pb and broaden the mammary glands when necessary. To keep this condition, the radiology technician pulls the hand and fixes the breast Pb using the compression face 22Btm of the compression plate 22. Accordingly, the positioning for CC projection is completed.

While the breast Pb of the subject P is fixed, a preparation operation of adjusting an irradiation field of X rays, inputting information indicating which of the right and left breasts corresponds to the breast Pb to be imaged, and the like is performed. If the irradiation field of X rays is adjusted, the X-ray path is also adjusted such that X rays pass through the transparent region tp of the compression face 22Btm.

After that, an image of the fixed breast Pb is picked up. The breast Pb is irradiated with X rays by a radiology technician's operation of the operating console. The breast Pb is irradiated with X rays that conform to the conditions such as a preset X-ray irradiation amount. The X-ray detector 5 of the imaging plane detects an X ray that has transmitted the breast Pb. If the X-ray detector 5 is an FPD, the detected X ray is converted into an electrical signal in the X-ray detector 5. The electrical signal is converted into projection data by a data collection circuit (not shown). The projection data is converted into image data of the breast Pb by an image processing circuit (not shown). The image data of the breast Pb is displayed on a display. Regarding the image data of the breast Pb, information indicating whether the target breast Pb is a right one or a left one is stored as associated information.

When the irradiation of the breast Pb of the subject P by X rays is completed, the compression mechanism 11 raises the compression plate 22 from the imaging table 6.

When the imaging of the breast Pb of the subject P is continued to pick up an image of the breast Pb in a different direction and pick up an image of the other breast Pb, a series of steps is repeated. If all images are picked up, the imaging is completed.

Imaging of the right breast in the MLO direction will be described here with reference to FIG. 9.

The X-ray diagnostic apparatus receives an instruction about the imaging direction (MLO direction) of the subject's breast from the radiology technician.

Then, the X-ray diagnostic apparatus reads information input by a radiology technician's operation of the operation panel 35 and adjusts the angle and height of the arm 21 in accordance with the imaging direction and the height of the breast.

Figure 9:
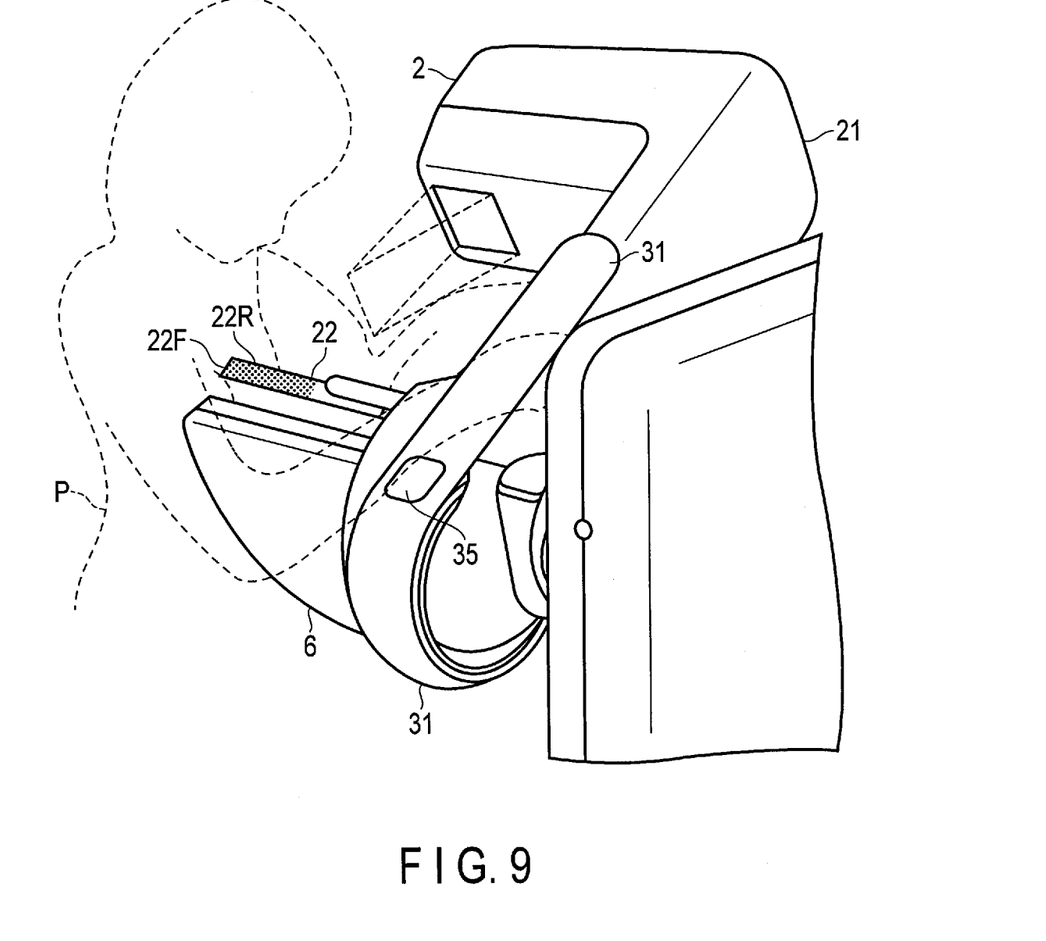
FIG. 9 is a schematic view illustrating an operation of the X-ray diagnostic apparatus according to the first embodiment.

When the imaging direction is the MLO direction, the radiology technician positions the breast of the subject P on the imaging table 6, as shown in, e.g., FIG. 9. During the positioning for MLO projection, the breast is caught between the compression plate 22 and the imaging plane, and the arm of the subject P is put on the arm rest 31 and the fingers thereof are hooked on the edge of the arm rest 31. In this state, the arm is bent and the chest wall is brought into contact with the compression plate 22 to move the compression plate 22 close to the imaging table 6.

Then, the chest wall face 22F of the compression plate 22 slides on the chest wall of the subject P and moves close to the imaging table 6. Thus, the subject p can be relieved of pain because the chest wall face 22F does not pull the skin of the chest wall downward.

Furthermore, the side face 22R of the compression plate 22 slides on the skin of the upper arm of the subject P and moves close to the imaging table 6 through the region r_R whose surface roughness is greater than that of the transparent region tp. On the side face 22R, the region r_R is not essential but can be excluded because it may not be in contact with the upper arm depending upon the posture of the subject P. The same holds true for the region r_L included in the other side face 22L.

After the compression plate 22 moves close to the breast Pb, the radiology technician puts his or her hand between the compression plate 22 and the breast Pb to flatten the breast Pb and broaden the mammary glands when necessary, as described above. To keep this state, the radiology technician pulls the hand and fixes the breast Pb using the compression face 22Btm of the compression plate 22. Accordingly, the positioning for MLO projection is completed.

As in the foregoing step, the preparation operation is performed and then the breast Pb is imaged. Similarly, a series of steps is repeated to continue imaging the breast Pb of the subject P. If all images are picked up, the imaging is completed.

As described above, according to the first embodiment, the compression plate includes a compression face opposed to the imaging table to compress the breast and a chest wall face which is formed continuously from the compression face and which is in contact with the chest wall of the subject during X-ray imaging. The chest wall face which is in contact with the chest wall includes a second region whose surface roughness is greater than that of a first region of the compression face, which is opposed to the imaging table.

Since, therefore, the chest wall face of the compression plate includes the second region whose surface roughness is greater than that of the first region, the compression plate does not stick to the skin of the chest wall of a subject, with the result that the subject can be relieved of pain while the compression plate is moving down. This advantage can be obtained even if the "step of moving the compression plate down" before CC projection is read as a "step of moving the compression plate close to the imaging table" before MLO projection.

Furthermore, according to the first embodiment, the side faces of the compression plate may include a third region whose surface roughness is greater than that of the first region of the compression face. In this case, the compression plate does not stick to the skin of the upper arm of the subject, with the result that the subject can be relieved of pain while the compression plate is moving down. In addition to this, the breast is hard to see from its sides; consequently, a sense of shame of the subject can be lessened.

According to the first embodiment, the first region of the compression face may include an X-ray path and at least one of each of the side faces and the compression face may include a fourth region whose surface roughness is greater than that of the first region. In this case, the subject can be relieved of pain as described above. When the side faces include a fourth region, a sense of shame of the subject can be lessened as described above. The region whose surface roughness is greater in the side faces is called "a third region" when it is described irrespective of the X-ray path, and it is called "a fourth region" when it is described in association with the X-ray path.

According to the first embodiment, the second and third regions can be formed continuously to each other. In this case, the compression plate does not stick to the skin between the chest wall of the subject and the upper arm thereof, with the result that the subject can be relieved of pain while the compression plate is moving down.

Moreover, according to the first embodiment, the side which is located on the border between the compression face and the chest wall face and which is in contact with the root of the breast, may include a fifth region whose surface roughness is greater than that of the first region at the roundish corner. In this case, the compression plate does not stick to the skin of the root of the breast, with the result that the subject can be relieved of pain while the compression plate is moving down.

As described above, according to the first embodiment, at least the second region that is likely to be in contact with skin other than the breast skin, is surface-treated to have a smooth, dry surface. Since, therefore, the compression plate sticks to no skin, the subject can be relieved of pain while the compression plate is moving down.

Furthermore, according to the first embodiment, the surface roughness of the second region may fall within a range of 0.1 μm to 2 μm. In this case, the surface roughness can be defined quantitatively. Thus, when part of a half-finished product the entire surface of which is transparent, is surface-treated to produce a compression plate, the quality of the surface treatment can be managed.

Furthermore, according to the first embodiment, the chest wall face can be made thinner than each of the side faces. In this case, an image of the root of the breast can be picked up while decreasing the degree of pulling out the breast for positioning.

Second Embodiment

Figure 10:
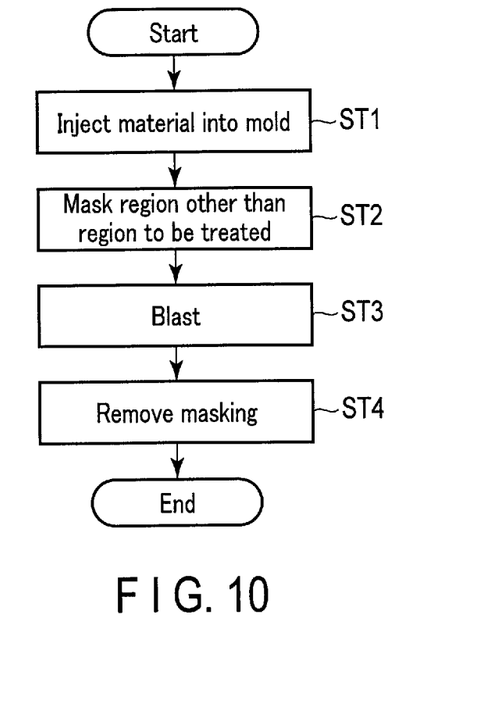
FIG. 10 is a flowchart illustrating a method of manufacturing a compression plate according to a second embodiment.

A method of manufacturing a compression plate for use in the foregoing X-ray diagnostic apparatus will be described using the flowchart shown in FIG. 10. With this method, the compression plate 22 according to the first embodiment can be manufactured. Below is a specific description of a method of manufacturing the compression plate 22.

First, a resin material is injected into a mold to form the compression plate 22 (step ST1). This molding can be called injector molding because a molten resin material is injected into a mold from an injector and then cooled to form a compression plate. As the resin material, for example, polycarbonate is used.

Subsequently, in the compression plate (a half-finished product whose surface has not been treated) removed from the mold after the resin material is cooled, a region other than a region to be blasted is masked (step ST2). When the chest face 22F is blasted, the compression face 22Btm to compress the breast to the imaging table 6 is masked irrespective of whether the side faces 22L and 22R and the back face 22Back are blasted. It is optional whether to blast the back face 22Back and it is also optional whether to mask it.

After that, the chest wall face 22F, which is formed continuously from the masked compression face 22Btm and brought into contact with the chest wall of the subject during X-ray imaging, is blasted (step ST3). In step ST3, a region r_F whose surface roughness is greater than that of the transparent region tp of the compression face 22Btm, which is opposed to the imaging table 6, is formed on the chest wall face 22F that is brought into contact with the chest wall Pw. In this blasting, as an abrasive to be sprayed onto the surface of resin, for example, fused alumina and silicon carbide can be used as appropriate. As the grain size of the abrasive, for example, F16 to F220 prescribed in the JIS R6001-1998 can be used as appropriate.

If the side faces 22L and 22R are not masked in step ST2, they are blasted in step ST3. Similarly, if the sides Sd1 to Sd8 or the tops A1 to A4 are not masked, they are blasted in step ST3. Similarly, the region r_B of the compression face 22Btm is not masked in step ST2, and is blasted in step ST3.

When the blasting is finished, the masking is removed (step ST4).

Accordingly, the foregoing compression plate 22 is completed.

As described above, according to the second embodiment, the compression plate manufacturing method includes injecting a resin material into a mold to form a compression plate and masking a compression face of the compression plate removed from the mold after the resin material is cooled, the compression face compressing the breast to the imaging table. The compression plate manufacturing method also includes blasting a chest wall face which is formed continuously from the masked compression face and brought into contact with the chest wall of the subject during X-ray imaging and removing the masking after the blasting. The blasting is to form a second region whose surface roughness is greater than that of a first region of the compression face which is opposed to the imaging table, on the face that is in contact with the chest wall of the chest wall face.

Therefore, in the manufacturing method using blasting according to the second embodiment, a compression plate that brings about the same advantages as those of the first embodiment can be manufactured.

Modification

A modification to the second embodiment will be described below.

In this modification, the compression plate manufacturing method uses a mold transfer in place of the foregoing blasting. More specifically, a compression plate 22 is manufactured by transferring a region (a minute uneven region), the surface roughness of which is greater than that of the transparent region tp, to thermoplastic resin using a mold that is surface-treated in advance. Below is a description of the modification using a flowchart shown in FIG. 11.

Figure 11:
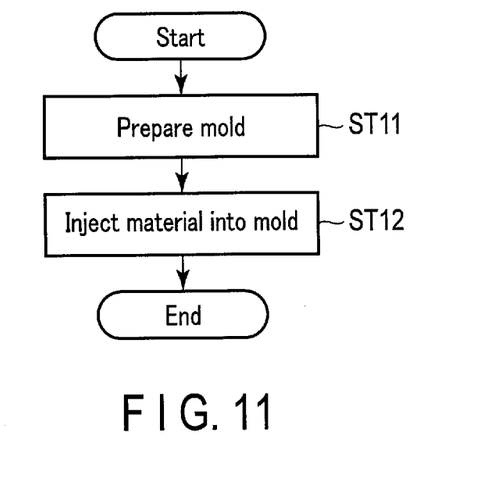
FIG. 11 is a flowchart illustrating another method of manufacturing the compression plate according to the second embodiment.

First, a mold is prepared to form a compression plate 22 including a compression face 22Btm to compress a breast to the imaging table 6 and a chest wall face 22F that is in contact with the chest wall of a subject during X-ray imaging (step ST11). The mold has a transfer face to form a region whose surface roughness is greater than the transparent region tp of the compression face 22Btm, which is opposed to the imaging table 6 so as to be in contact with the chest wall of the chest wall face 22F. The mold may include a transfer face whose surface roughness corresponds to the side faces 22L and 22R, sides Sd1 to Sd8 and tops A1 to A4 as appropriate, as well as the transfer face whose surface roughness corresponds to the chest wall face 22F.

Subsequently to step ST11, a resin material is injected into a mold to form the compression plate 22 (step ST12). Step ST12 includes a step of forming a region r_F on the transfer face of the mold in contact with the chest wall. In accordance with the transfer face of the mold, step ST12 includes a step of forming a region whose surface roughness corresponds to the side faces 22L and 22R, sides Sd1 to Sd8 and tops A1 to A4 on the resin material.

Subsequently to step ST12, the resin material is cooled and then the compression plate 22 is removed from the mold. Accordingly, the compression plate 22 is completed.

According to the modification as described above, a compression plate 22 that brings about the same advantages as those of the first embodiment can be manufactured even though a mold whose surface is treated in advance is used in place of the blasting.

In addition to the above, according to the modification using a mold, for example, the region r_R in the chest wall face 22F and the regions r_L and r_R in the side faces 22L and 22R can be formed to have different surface roughnesses. Thus, the surface roughness of each of the regions of the compression plate 22 can be adjusted in accordance with the sensitiveness of skin of the chest wall and the upper arms of the subject.

The transparent region tp of each of the embodiments is one example of the first region recited in the claims. The region r_F of each of the embodiments is one example of the second region recited in the claims.

The regions r_L and r_R of each of the embodiments are one example of the third region recited in the claims. The regions r_L, r_R and r_B of each of the embodiments are one example of the fourth region recited in the claims. The side Sd2 and the region r_2 of each of the embodiments are one example of the side (which is in contact with the root of a breast) and the fifth region recited in the claims.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A compression plate to compress a breast of a subject with the breast between the compression plate and an imaging plane of an imaging table, the compression plate comprising:
    a compression face configured to compress the breast to the imaging table; and
    a chest wall face configured continuously from the compression face to be in contact with a chest wall of the subject during X-ray imaging,
    wherein the chest wall face includes a second region which is in contact with the chest wall of the subject, and the second region has surface roughness which is greater than that of a first region of the compression face, which is opposed to the imaging table.

2. The compression plate according to claim 1, further comprising a plurality of side faces configured continuously from the compression face and the chest wall face along a direction orthogonal to the compression face and the chest wall face,
    wherein the side faces each include a third region whose surface roughness is greater than that of the first region.

3. The compression plate according to claim 1, further comprising a plurality of side faces configured continuously from the compression face and the chest wall face along a direction orthogonal to the compression face and the chest wall face,
    wherein the first region includes an X-ray path; and
    at least one of each of the side faces and the compression face includes a fourth region whose surface roughness is greater than that of the first region.

4. The compression plate according to claim 2, wherein the second region and the third region are configured continuously from each other.

5. The compression plate according to claim 1, further comprising a side located on a border between the compression face and the chest wall face in contact with a root of the breast, the side including a fifth region whose surface roughness is greater than that of the first region at a roundish corner.

6. The compression plate according to claim 1, wherein the surface roughness of the second region falls within a range of 0.1 μm to 2 μm.

7. The compression plate according to claim 2, wherein the chest wall face is thinner than each of the side faces.

8. An X-ray diagnostic apparatus comprising:
    the compression plate according to claim 1; and
    the imaging table having the imaging plane.

9. A method of manufacturing a compression plate to compress a breast of a subject with the breast between the compression plate and an imaging table, the method comprising:
    injecting a resin material into a mold to form the compression plate;
    masking a compression face of the compression plate to compress the breast to the imaging table, the compression plate being removed from the mold after the resin material is cooled;
    blasting a chest wall face configured continuously from the masked compression face to be in contact with a chest wall of the subject during X-ray imaging; and
    removing the masking after the blasting,
    wherein the blasting being forming a second region whose surface roughness is greater than that of a first region of the compression face, which is opposed to the imaging table, on a face that is in contact with the chest wall of the chest wall face.

10. A method of manufacturing a compression plate to compress abreast of a subject with the breast between the compression plate and an imaging table, the method comprising:
    preparing a mold to form a compression plate including a compression face configured to compress the breast to the imaging table and a chest wall face configured continuously from the compression face to be in contact with a chest wall of the subject during X-ray imaging; and
    injecting a resin material into the mold to form the compression plate,
    wherein:
    the preparing includes preparing a mold having a transfer face to form a second region whose surface roughness is greater than that of a first region of the compression face, which is opposed to the imaging table, on a face that is in contact with the chest wall of the chest wall face; and
    the injecting includes forming the second region on a face that is in contact with the chest wall by the transfer face.

\* \* \* \* \*